United States Patent [19]
Robbins

[11] 3,991,215
[45] Nov. 9, 1976

[54] MANUFACTURE OF YEAST PROTEIN ISOLATE HAVING A REDUCED NUCLEIC ACID CONTENT BY A THERMAL PROCESS

[75] Inventor: Ernest Aleck Robbins, High Ridge, Mo.

[73] Assignee: Anheuser-Busch, Incorporated, St. Louis, Mo.

[22] Filed: Feb. 11, 1974

[21] Appl. No.: 441,118

[52] U.S. Cl. ............................. 426/60; 426/656; 195/5; 260/112 R
[51] Int. Cl.$^2$ ............................................ A23J 1/18
[58] Field of Search .......... 426/148, 204, 60, 364, 426/656; 260/112 R; 195/4, 5

[56] References Cited
UNITED STATES PATENTS

| | | |
|---|---|---|
| 3,775,393 | 11/1973 | Akin et al. .................. 260/112 R |
| 3,867,255 | 2/1975 | Newell et al. ..................... 195/5 |
| 3,867,554 | 2/1975 | Sucher et al. .................... 426/60 |
| 3,867,555 | 2/1975 | Newell et al. .................... 426/60 |

*Primary Examiner*—A. Louis Monacell
*Assistant Examiner*—Ester L. Massung
*Attorney, Agent, or Firm*—Gravely, Lieder & Woodruff

[57] ABSTRACT

This application involves a process of reducing nucleic acid (RNA) in yeast products by heating the protein containing portion of the yeast to over 100° C. for 10 seconds to 60 minutes at a pH of about 6 to about 8. A novel yeast cell wall low RNA protein product is disclosed as is a low RNA protein isolate.

14 Claims, 2 Drawing Figures

MANUFACTURE OF YEAST PROTEIN ISOLATE HAVING A REDUCED NUCLEIC ACID CONTENT BY A THERMAL PROCESS

REFERENCE TO PRIOR APPLICATIONS

This application contains subject matter in common with one or more of the following copending applications owned by the assignee of this invention: Sucher et al U.S. Pat. No. 3,867,554 issued Feb. 18, 1975; Robbins et al U.S. Pat. No. 3,887,431 issued June 3, 1975; Newell et al U.S. Pat. No. 3,867,255 issued Feb. 18, 1975; Newell et al U.S. Pat. No. 3,867,555 issued Feb. 18, 1975; Newell et al U.S. Pat. No. 3,888,839 issued June 10, 1975; and Robbins et al Ser. No. 349,316.

BACKGROUND OF THE INVENTION

There has been considerable information published on the production of microbial protein. The term 'microbial protein' has developed two meanings. One meaning connotes the whole cell, in which the protein is contained within the confines of the cell wall and therefore is relatively nonfunctional. The other meaning connotes a protein isolated as a separate entity from the microbe. In either case, for human nutrition, the nucleic acid content of the protein product should be reduced to below 9 percent if a substantial amount of yeast protein is used in the human diet. The Recommended Daily Allowance of The Food and Nutrition Board, National Research Council for protein is 65 grams per day for a 70 kilogram adult male and The Protein Advisory Group of the United Nations System recommends that the amount of nucleic acid ingested per day from microbial protein should be less than two grams. Therefore, the nucleic acid content of the protein should be less than 3 percent if these criteria are to be met when yeast protein is the only source of dietary protein. The nucleic acid content should be less than 6 percent if the yeast protein constitutes 50 percent of the dietary protein.

The nucleic acid content of yeast cells such as *Candida utilis* and *Saccharomyces cerevisiae* is about 12 to 15 grams of nucleic acid per 100 grams of crude protein. Crude protein is calculated in this application as the Nitrogen (N) content multiplied by 6.25. The protein isolated from these cells also contains 12 to 15 grams nucleic acid per 100 grams of crude protein. Thus, the nucleic acid content must be reduced substantially, up to four to five fold, before the protein can be considered as acceptable as the sole source of protein for human nutrition. The nucleic acid of yeast is mainly ribonucleic acid or RNA, and in this application these terms will be used interchangeably.

The reduction of the nucleic acid content can be accomplished by the hydrolysis of the nucleic acid within the cell to fragments of such size that the fragments can be diffused from the cell away from the protein. It is known that the enzyme, nuclease, is present in certain yeast cells and that nuclease hydrolyzes or breaks up nucleic acid molecules to smaller fragments. It also is known in the art that the hydrolysis of nucleic acids within the cell can be accomplished by a multi-step heating process to activate the self-contained or endogenous nuclease to produce cells containing two to three grams of nucleic acid per 100 grams of protein. Nucleic acid also can be hydrolyzed by exposing the cell to an external nuclease. It is further known in the art that alkali can be used to extract nucleic acid from yeast cells.

In any of these procedures, two fractions are obtained. One fraction is the cell containing a reduced content of nucleic acid. The other fraction is the surrounding medium containing nucleic acid fragments and other diffusable material. One disadvantage of these processes is that the protein remains within the cell in a non-functional form for food use. Another disadvantage is that the processes by which the cell wall is made permeable to the nucleic acid fragments also severely decrease the ability of the cell to be ruptured to allow the protein to be harvested. A further disadvantage is the difficulty in controlling the endogenous protease which hydrolyzes the protein, thereby complicating protein recovery.

When yeast cells from which the RNA has not been separated are ruptured by any method, a cellular debris fraction and a soluble cytoplasmic constituent fraction are obtained. These fractions can be separated by centrifugation or filtration. Among the soluble cytoplasmic constituents are the nucleic acid and the protein, either individually or in conjugation. In any situation, recovery of the protein by isoelectric precipitation results in a protein product with an undesirable content of nucleic acid.

We have discovered a process by which thermal energy can be used to prepare a protein product having a reduced nucleic acid content in good yield from yeast. The protein product also has desirable functional characteristics. The heat treatment process steps may be applied at any of several places in the process used to produce yeast protein. The heat treatment of this invention may be applied effectively to ruptured yeast cells; to the soluble cytoplasmic fraction from ruptured yeast cells; or to recovered isolated protein product. In each of these instances, the RNA is effectively separated from the protein.

Another advantage of this process is that the protein can be recovered without additional treatment. A third advantage is that the cell walls of yeast can be recovered as a separate valuable product. Still another advantage is that the non-protein solubles cytoplasmic constituents can be recovered and processed to a valuable product. Because of the severity and extent of the heat treatment, a still further advantage of this invention is that the protein and the soluble constituents are recovered free of microorganisms, i.e., are sterile.

DETAILED DESCRIPTION

Figure 2:
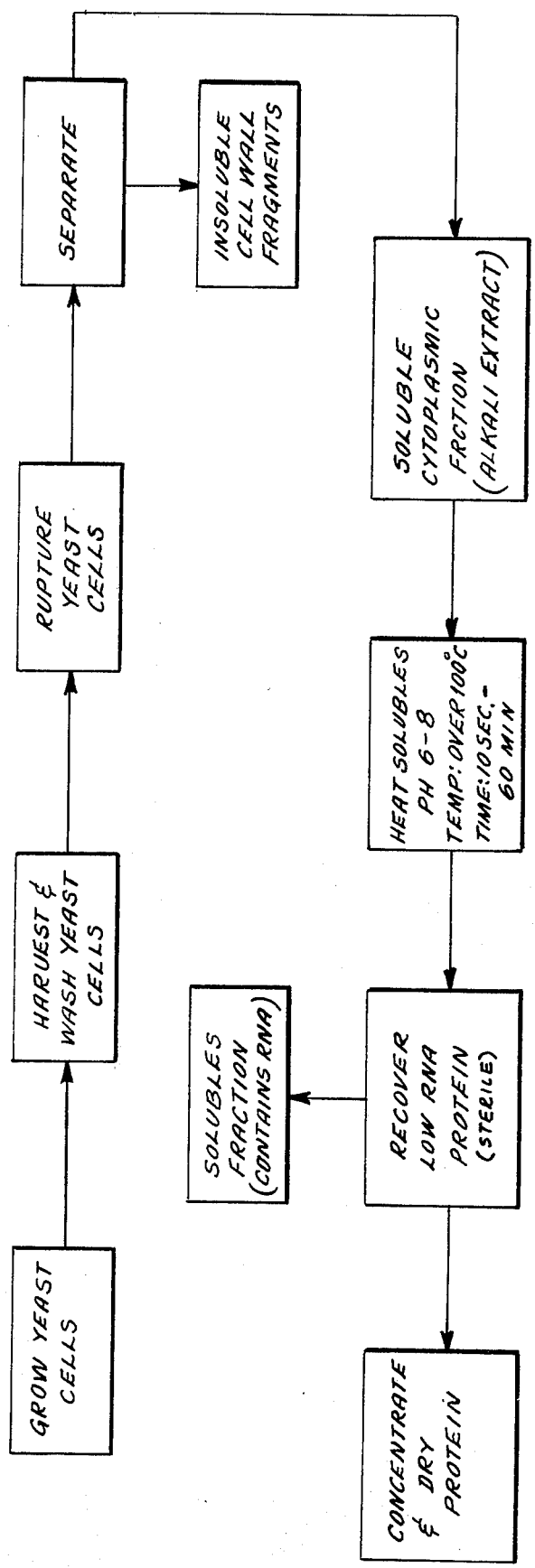
FIG. 2 is a flow diagram of the preferred process of this invention.

Our primary process in its preferred form as shown in detail in FIG. 2 is comprised of the following steps: production of yeast cells, rupture of the cells, separation of the insoluble cell wall fragments from the soluble cytoplasmic fraction, treatment of the soluble fraction with heat (UHT), recovery of the low nucleic acid protein by centrifugation, vacuum concentration, and drying.

Figure 1:
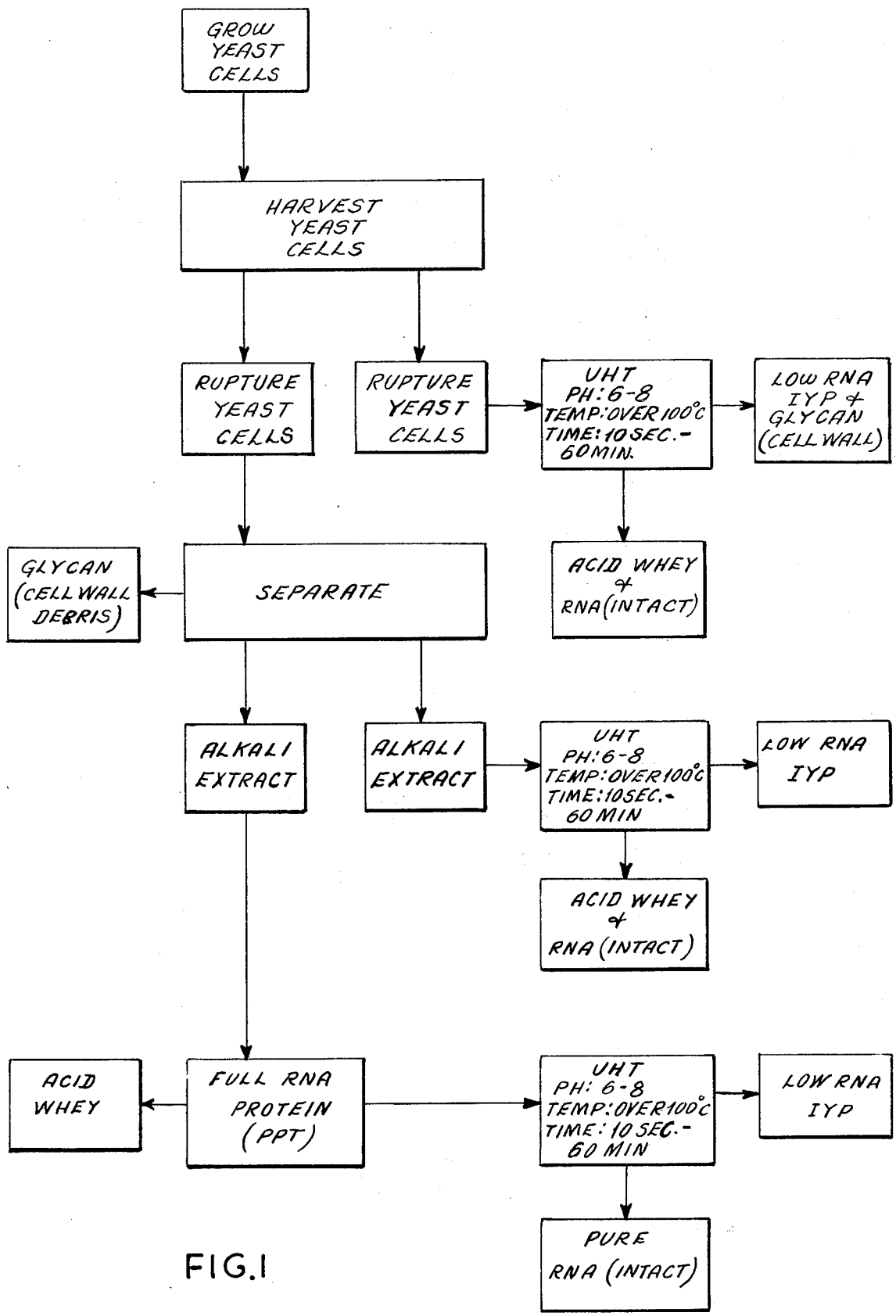
FIG. 1 is a flow diagram of the overall process showing the various places where the heat treatment can be applied.

However, the heat treatment (UHT), as shown in FIG. 1, may be applied directly to the ruptured yeast cells which results in the production of the following end products:
1. an acid whey or yeast extract which contains the RNA;
2. a low RNA protein (IYP) plus the cell walls or glycan.

Another alternative (preferred) process is to apply the heat treatment (UHT) to the alkali extract after the cell wall debris (glycan) has been separated therefrom. Applying the heat treatment at this stage in the process results in the following three end products: (1) cell wall debris; (2) acid whey containing RNA; (3) a low RNA protein (IYP).

A third alternative process is to precipitate the full RNA protein from the alkali extract and then apply the heat treatment to the full RNA protein. This process produces the following four end products: (1) cell wall debris; (2) acid whey (extract); (3) pure RNA; (4) low RNA protein.

In all of these procedures, the RNA is recovered in relatively intact form, i.e., the molecule is not degraded.

PREFERRED PROCESS

Yeast cells (biomass) are produced by methods known to those versed in the art. We preferably use biomass of strains of Saccharomyces and Candida grown on food grade nutrients in batch and continuous fermentation. However, the main considerations are that the yeast be of food grade and produced in good yield.

The biomass is harvested by centrifugation or filtration, and water washed. When necessary, dilute alkali may be incorporated into the wash to remove adhering color and taste bodies. The yeast cells are ruptured by any of several known methods, such as, high pressure homogenization, attrition in a sand or colloid mill, sonic disintegration, repeated freeze-thaw cycles, lytic enzymes, and the like. The main consideration is to rupture the majority of cells under such conditions that the majority of the non-cell wall materials remain in the soluble state to facilitate removal from the cell walls. The ruptured cell system (homogenate) may be diluted, warmed and pH adjusted to favor processability.

The homogenate is separated by centrifugation and/or filtration into a cell wall residue and an extract usually referred to as the alkali extract. The cell wall residue is further processed to glycan as described in Sucher et al co-pending application entitled YEAST GLYCAN AND PROCESS OF MAKING SAME, Ser. No. 310,452, now U.S. Pat. No. 3,867,554 issued Feb. 18, 1975.

The alkali extract is adjusted to pH 6–8 and rapidly heated to temperatures greater than 100° C. for up to 60 minutes, preferably 10 seconds to 5 minutes. This heating step separates the nucleic acid moiety from the protein of the nucleoprotein and insolubilizes the majority of the protein while the nucleic acid moiety remains soluble. It also sterilizes the solubles fraction and the fraction which is insolubilized. The insoluble protein is recovered by centrifugation and/or filtration, water washed, and dried. The insoluble protein slurry may be concentrated in vacuo before drying. The recovered sterile protein has a low RNA content. The composition (dsb) is: 75–92 percent crude protein, 0.5–5.0 percent RNA, 10–15 percent lipid, 1–5 percent ash, and 3–10 percent carbohydrate.

The solubles obtained by the removal of the insoluble protein is called acid whey or yeast extract. These solubles contain a minority of the cellular protein, the majority of the intact nucleic acid, part of the carbohydrate, and all of the constituents of the metabolic pools. The conversion of the acid whey to flavorful yeast products is described in co-pending application of Robbins et al Ser. No. 349,316 entitled EXTRACT OF YEAST AND PROCESSES OF MAKING SAME, now U.S. Pat. No. 3,914,450 issued Oct. 21, 1975.

Cell rupture, extraction of solubles, and processability are affected by pH, temperature, time, solids concentration, and homogenizer efficiency. Our usual method of measuring the extent of cell rupture is to determine the amount of nitrogen that remains soluble as follows:

$$\% \text{ N Extractability} = \frac{100 \times \text{g. N in supernate after centrifugation}}{\text{g. N homogenate before centrifugation}}$$

The RNA is determined by the following method:

RNA determination: About 50 mg. IYP is digested with 5 ml. of 0.2 N KOH for 30 minutes at 100° C. The digest is acidified with 5 ml. HClO$_4$ citrate reagent (0.4M citrate buffer, pH 2.2 containing 1.7 ml., 70% HClO$_4$ per 100 ml.). The residue is removed by centrifugation. The A$_{260}$ of the suitably diluted supernatant is measured. The extinction coefficient of 31.7 A$_{260}$ ml./mg. is used to calculate RNA. The RNA content is corrected for the A$_{260}$ contribution of protein fragments in the hydrolysate as measured by the Lowry method.

The crude protein is calculated from the Kjeldahl Nitrogen method, considering that the crude protein contains 16.0% nitrogen. The total nitrogen of the IYP is measured and multiplied by a factor of 6.25. The nucleic acid is considered to contain 16.3 percent nitrogen. Therefore, the RNA content divided by 6.13 gives the nitrogen content of the nucleic acid.

As an example, where RNA is measured to be 8.5 and total nitrogen is 13.92, then the calculations are made as follows:

Crude Protein = 13.92 × 6.25 = 87.0

$$\text{RNA Nitrogen} = \frac{\text{RNA}}{6.13} = \frac{8.5}{6.13} = 1.36$$

Corrected Protein = 6.25 × (13.92 − 1.36) = 78.4%

The yeast biomass after washing has a pH of 4.5–6.5. The biomass is usually chilled, then passed through a Manton-Gaulin homogenizer to a chilled receiver. The process is repeated for a total of three passes. At least three passes are needed to obtain maximum cell rupture. In practice, the biomass was homogenized at the ambient pH of the yeast, namely, 4.5–6.5. Cell rupture can also be achieved at a higher pH, up to at least pH 9.5, but the subsequent separation of the cell wall residue from the solubles becomes more difficult.

The effects of pH, solids concentration, and homogenizer efficiency upon the N extractability of Candida utilis and on Saccharomyces cerevisiae are shown in Table I and Table II.

The data of Table I and II show that extraction of the soluble nitrogenous materials can be carried out at least over the pH range of about 5.5 to about 11. Process considerations further limit the extraction pH to the range of about 7 to about 10, with pH 9.5 considered the optimal balance between extraction and subsequent separation of the cell wall residue from the solubles. Extraction is best at a low solids content, but again a consideration of process rates led to the adoption of a solids content of about 2.5 to about 4 percent. Extraction time can be varied between about 5 and about 60 minutes at extraction temperature of about 0° C. to about 60° C., preferably 25°–60° C. The best process rate for the subsequent separation of the cell wall residue from the solubles is obtained when the extraction is done at 60° C., for 5 to 20 minutes, at pH 9.5. When *Candida utilis* and *Saccharomyces cerevisiae*, each pass from 1 to 5 through the homogenizer improves the nitrogen extractability, presumably by rupturing more cells. A three pass system has been adopted as a good balance between efficiency of processing and cost. The pressure is between 5000 and 15000 psig. The temperature is between 0° and 60° C. The pH is 4.5 to 6.5.

Taking N extractability and processing requirements into consideration, the optimal process to obtain the insoluble cell wall material is: (1) growing a food grade yeast on a nutrient media, (2) harvesting and washing the yeast cells, (3) rupturing the yeast cells at a temperature of 0°–10° C., (4) handling the ruptured cells at a pH 9.5, at 60° C. for twenty minutes, and (5) removing the yeast insolubles at a temperature of about 60° C. The extract containing the soluble part of the yeast is called the alkali extract. Under the optimal conditions, 85–90 percent of the Kjeldahl N of the homogenate is obtained in the alkali extract. The highest N extractability will result in the lowest protein content of the glycan, and the highest protein content in the alkali extract.

TABLE I

Effect of Extraction pH, Solids Level, and Homogenizer Efficiency Upon Nitrogen Extractability of *Candida utilis*

Chilled suspensions of *Candida utilis* at pH 5.0–5.5, 7–10 % solids were homogenized by means of Manton-Gaulin homogenizer. The chilled homogenate was recycled through the homogenizer repeatedly to give one, two, three or four pass homogenate. The homogenate was diluted with up to 2.0 parts of water, and adjusted in pH. The diluted homogenates were incubated for 30 min. at 50° C. and then centrifuged. The nitrogen contents of the diluted homogenate, and of the supernate were measured by the Kjeldahl method. % N extractions were calculated.

| pH of Extraction | Solids Content | No. of Passes | % Nitrogen Extracted |
|---|---|---|---|
| 7 | 2.5 | 3 | 76* |
| 8 | 2.5 | 3 | 74* |
| 9 | 2.5 | 3 | 84* |
| 10 | 2.5 | 3 | 82** |
| 11 | 2.5 | 3 | 80** |
| 9.5 | 2.5 | 1 | 70* |
| 9.5 | 2.5 | 2 | 83* |
| 9.5 | 2.4 | 3 | 89* |
| 9.5 | 2.5 | 4 | 91* |
| 9 | 2.4 | 3 | 83* |
| 10 | 2.4 | 3 | 82** |
| 11 | 2.4 | 3 | 78** |
| 12 | 2.4 | 3 | 85** |
| 9 | 6.9 | 3 | 64** |
| 10 | 6.9 | 3 | 59*** |
| 11 | 6.9 | 3 | 54*** |
| 12 | 6.9 | 3 | 41*** |

Good (*), Medium (), or Poor (*) separation of cell wall residue and solubles.

TABLE II

Effect of Extraction pH, Temperature, Time, Solids Content, and Homogenizer Efficiency Upon the Nitrogen Extractability of *Saccharomyces cerevisiae*.

Chilled suspensions of commercial baker's yeast at ambient pH of 6–6.5, 7–10 % solids, were homogenized by means of a Manton-Gaulin homogenizer. The chilled homogenate was recycled through the homogenizer to give one, two or three passes. The homogenates were diluted with up to two volumes of water and adjusted in pH. The diluted homogenates were incubated for 5–60 minutes at 25–60° C. and centrifuged. The nitrogen contents of the homogenates and supernates after centrifugation were measured by the Kjeldahl method. % N extractions were calculated.

| pH | % Solids Content | Time (min.) | ° C. Temp. | No. of Passes | % Nitrogen Extractability |
|---|---|---|---|---|---|
| 9.5 | 9.1 | 30 | 25 | 3 | 83 |
| 9.5 | 4.8 | 30 | 25 | 3 | 84 |
| 9.5 | 3.1 | 30 | 25 | 3 | 92 |
| 9.5 | 3.1 | 30 | 25 | 2 | 80 |
| 9.5 | 3.1 | 30 | 25 | 1 | 63 |
| 9.5 | 3–4 | 5 | 50 | 3 | 91 |
| 9.5 | 3–4 | 20 | 50 | 3 | 93 |
| 9.5 | 3–4 | 30 | 50 | 3 | 96 |
| 9.5 | 3–4 | 60 | 50 | 3 | 96 |
| 9.5 | 3–4 | 5 | 60 | 3 | 93 |
| 9.5 | 3–4 | 20 | 60 | 3 | 94 |

TABLE II-continued

Effect of Extraction pH, Temperature, Time, Solids Content, and Homogenizer Efficiency Upon the Nitrogen Extractability of *Saccharomyces cerevisiae*.

Chilled suspensions of commercial baker's yeast at ambient pH of 6–6.5, 7–10 % solids, were homogenized by means of a Manton-Gaulin homogenizer. The chilled homogenate was recycled through the homogenizer to give one, two or three passes. The homogenates were diluted with up to two volumes of water and adjusted in pH. The diluted homogenates were incubated for 5–60 minutes at 25–60° C. and centrifuged. The nitrogen contents of the homogenates and supernates after centrifugation were measured by the Kjeldahl method. % N extractions were calculated.

| pH | % Solids Content | Time (min.) | ° C. Temp. | No. of Passes | % Nitrogen Extractability |
|---|---|---|---|---|---|
| 9.5 | 3–4 | 30 | 60 | 3 | 91 |
| 9.5 | 3–4 | 60 | 60 | 3 | 90 |
| 4.0 | 3–4 | 30 | 25 | 3 | 33 |
| 5.0 | 3–4 | 30 | 25 | 3 | 36 |
| 6.0 | 3–4 | 30 | 25 | 3 | 79 |
| 7.0 | 3–4 | 30 | 25 | 3 | 93 |
| 8.5 | 3–4 | 30 | 25 | 3 | 93 |
| 9.5 | 3–4 | 30 | 25 | 3 | 96 |
| 6.0 | 3–4 | 60 | 60 | 3 | 42 |
| 6.5 | 3–4 | 60 | 60 | 3 | 33 |
| 7.5 | 3–4 | 60 | 60 | 3 | 30 |
| 8.5 | 3–4 | 60 | 60 | 3 | 73 |
| 9.5 | 3–4 | 60 | 60 | 3 | 90 |

The alkali extract contains all of the cellular constituents except the cell wall component, which is the cellular debris or cell wall debris. That is, the alkali extract contains high molecular weight protein, nucleic acid, fat, and carbohydrate, as well as the low molecular weight constituents of the metabolic pools such as amino acids, peptides, nucleotides, nucleosides, nitrogen bases, glycolytic pathway intermediates, vitamins, minerals, and the like. The majority of the protein and the majority of the nucleic acid are in combination as a nucleoprotein.

If the protein is recovered by isoelectric precipitation as described in co-pending application of Newell et al Ser. No. 310,455 entitled ISOLATED YEAST PROTEIN PRODUCT WITH INTACT RNA AND A PROCESS FOR MAKING SAME, now U.S. Pat. No. 3,888,839, issued June 10, 1975, then the isolated protein contains a relatively high content of nucleic acid and is referred to as full RNA-IYP. However, if the alkali extract is thermally treated in accordance with the conditions of this invention before recovery of the protein, then the recovered protein product has a low level of nucleic acid and is referred to as low RNA-IYP. When the alkali extract is treated in accordance with this invention, then the low RNA-IYP is insolubilized and may be recovered with or without additional pH adjustment.

Factors that affect the utilization of thermal energy to produce the low RNA-IYP are temperature, duration of heating, pH, and solids contents of the alkali extract. Data relevant to the effect of these factors are presented in Tables III–VII.

TABLE III

Effect of Process and Harvest pH on Protein Structure, Yield, Composition, and Flavor An alkali extract of baker's yeast was prepared according to Example 1. The alkali extract contained 2.76 % total solids of which 65 % was crude protein. Aliquots of the alkali extract (200 ml.) were adjusted to the noted pH's with strong NaOH or HCl, heated at 118–125° C. for 60 minutes, and cooled. The protein structure was noted. In most cases, the samples were adjusted to pH 4.5 with HCl and centrifuged. The recovered protein was washed once and analyzed.

| Test | Process Conditions | | | Harvest pH | Yield | % Composition(dsb) | | Curd Structure | Color | Aroma |
|---|---|---|---|---|---|---|---|---|---|---|
| | pH | Temp. | Time | | | RNA | Crude Protein | | | |
| 53 | 9.5 | 120° C. | 60' | 4.5 | 66 | 2.6 | 83 | None | Dark | Sulfur |
| 54 | 8.5 | " | " | " | 73 | 4.3 | 85 | loose gel | Dark | Sl. Sulfur |
| 55 | 7.5 | " | " | " | 74 | 5.6 | 89 | gel | White | Near Bland |
| 56A | 6.5 | " | " | " | 80 | 7.8 | 86 | firm gel | Dark | Sl. Popcorn |
| 56B | 6.5 | " | " | 6.5 | 67 | 0.8 | 85 | firm gel | White | Near Bland |
| 57 | 5.5 | " | " | 4.5 | 82 | 12.2 | 85 | firm gel | White | Burnt, sulfur |
| 58 | 4.5 | " | " | 4.5 | 81 | 14.1 | 90 | firm gel | White | Burnt sulfur |
| 59 | 9.5 | 30° C. | 15' | 4.5 | 85 | 13.3 | 89 | | | |

Test No. 59 of Table III shows the high RNA content of a full RNA-IYP. Tests Nos. 53 to 58 (except No. 56B) shows that an increasing cook pH causes a decrease in the RNA content of the protein recovered at pH 4.5. At a pH of 9.5, and to some extent at pH 8.5, adjustment to pH 4.5 is necessary to insolubilize the protein. At pH's below 8.5, a firm gel formed on cooking. However, test No. 56B shows that at the cook pH of 6.5 the protein recovered without pH adjustment was of low RNA content. Furthermore, the protein recovered from No. 56B was white in color and nearly bland in aroma. At higher pH's (8.5 and 9.5) and lower pH's (5.5 and 4.5), the sulfur odor indicates decomposition of the sulfur containing amino acids. Inasmuch as the sulfur containing amino acids are nutritionally limiting in yeast protein, any decrease in their content decreases the protein quality.

The effect of the duration of heating is shown in Example 2. In this example, the RNA content had nearly reached a minimum in the 13 minutes that were needed to reach 118° C. A further study of the effect of duration of heating was provided by the use of a continuous heating system as described in Example No. 3. This system showed that a duration of two minutes at 110°–115° C., pH 6.5 decreased the RNA content of the harvested protein to 2.0 percent. A duration of 5.3 minutes further reduced the RNA to 1.6 percent dsb.

The effect of temperature on the process is shown in Table IV.

TABLE IV

Effect of Process Temperature on Protein Composition and Yield

Alkali extract of baker's yeast was treated in the continuous heating system as described in Example No. 3 except that the temperature of incubation was varied during the experiment.

| Test No. | Process Temp. (° C.) | % RNA | Protein Composition (dsb) % Crude Protein | %[2] Yield |
|---|---|---|---|---|
| 61 | 45 | 8.5 | 87 | 36 |
| 62 | 57 | 3.3 | 89 | 57 |
| 63 | 65 | 6.9 | 88 | 64 |
| 64 | 74 | 7.7 | 86 | 68 |
| 65 | 82 | 6.9 | 89 | 68 |
| 66 | 88 | 7.4 | 90 | 71 |
| 67 | 94 | 6.9 | 91 | 65 |
| 68 | 101 | 4.9 | 89 | 62 |
| 69 | 109 | 4.9 | 88 | 63 |
| 70 | 115 | 3.6 | 87 | 62 |
| 71 | 126 | 3.4 | 87 | 60 |
| 60 | 126 | 3.4 | 87 | 60 |
| 60[1] | X | 11.3 | 83 | 59 |

[1] A full RNA-IYP obtained by adjusting a portion of the alkali extract to pH 4.5 and recovering the protein.

[2] % Yield = $100 \times \frac{\text{g. N recovered in IYP}}{\text{g. N alkali extract}}$ Test No. 60 of Table IV shows that the full RNA-IYP contained 11.3 percent RNA. Test No. 62 shows that the incubation of the extract at pH 6.5 for two minutes at 57° C. decreased the RNA content of the recovered protein. This reduction is the result of the action of endogenous nuclease as described in Robbins et al co-pending application Ser. No. 310,469 entitled YEAST PROTEIN ISOLATE WITH REDUCED NUCLEIC ACID CONTENT AND PROCESS OF MAKING SAME now U.S. Pat. No. 3,887,431, issued June 3, 1975.

The nuclease rapidly becomes inactive as the temperature is increased as evidenced by the increasing content of RNA in the recovered protein. The RNA content of the isolated protein is constant as the temperature is increased above 65° C. until a temperature of greater than 100° C. is reached. The RNA content of the IYP becomes less as the temperature is increased to 126° C. The crude protein content of the IYP is constant at 87–90 percent (dsb). The yield of crude protein decreases as the RNA content of the IYP becomes less. However, the correction for the RNA harvested with the protein shows that the yield of corrected protein is essentially constant.

The data of Table V shows that a small amount of calcium ion added to the alkali extract causes a decreased RNA content in the IYP. These data further demonstrate the efficiency of process temperatures greater than 100° C.

TABLE V

Effect of Process Temperature and Added Calcium Ion IYP Composition

Alkali extract was prepared in accordance with Example No. 1. The alkali extract contained 2.67 % total solids. The alkali extract was adjusted to pH 6.5 by the addition of sodium hydroxide. Aliquots were adjusted to 0, 0.001, and 0.005 molar calcium chloride and heated at 100° C. and 120° C. for one hour. The IYP was recovered and analyzed.

| Test No. | Moles of $CaCl_2$ | Process Temp. ° C. | IYP Composition (dsb) RNA | Crude Protein |
|---|---|---|---|---|
| 72 | 0 | 121 | 2.1 | 85 |
| 73 | 0.001 | 121 | 1.4 | 85 |
| 74 | 0.005 | 121 | 1.6 | 86 |
| 75 | 0 | 100 | 4.2 | 87 |
| 76 | 0.001 | 100 | 4.1 | 86 |
| 77 | 0.005 | 100 | 4.6 | 85 |

Although the data of Tables I–V were obtained with baker's yeast, our process is not limited to baker's yeast. As shown in Table VI the process is applicable to various species of yeast.

TABLE NO. VI

The Nucleic Acid Content of IYP Prepared from Various Yeasts

Yeast biomass was prepared in fermentation by processes known to those versed in the art. The yeast biomass was harvested by centrifugation and washed twice with water. The yeast cells were ruptured by means of a Manton-Gaulin homogenizer. Protein and other solubles were extracted from the homogenate by stirring at pH 9.5 and recovered as an alkaline extract by centrifugation. The extraction and centrifugation were conducted at 25° C. A portion of the alkaline extract was immediately adjusted to pH 4.5 to precipitate a full RNA-IYP. Another portion of the alkaline extract was acidified to pH 7, and heated at 120° C. for one hour. The insoluble protein was recovered by centrifugation. The IYP's were water washed and analyzed for RNA content.

| Test No. | Yeast Source | Growing Conditions | % RNA in the IYP (dsb) No treatment | Thermal Process |
|---|---|---|---|---|
| 78 | Saccharomyces carlsbergensis | spent yeast recovered from brewer's wort | 7.6 | 2.3 |
| 79 | Saccharomyces carlsbergensis | batch fermentation on molasses | 13.4 | 0.8 |
| 80 | Saccharomyces elipsoideus (Montrechet) | '' | 13.9 | 0.8 |
| 81 | '' '' (Steinberg) | '' | 13.4 | 0.8 |
| 82 | Candida utilis Y900 | '' | 12.5 | 0.9 |
| 83 | Candida utilis Y1084 | '' | 12.2 | 1.1 |

All of the yeasts show nearly total reduction of the RNA content of the IYP. Furthermore, the low RNA-IYP from the various yeasts are obtained in reasonable yield and with comparable compositions as shown in Table VII.

TABLE VII

IYP Composition and Yield Obtained by the Thermal Process On Further Analysis of Various Yeasts of Table VI

| IYP of Test No. | Protein Crude | Protein Corrected | RNA | Ash | Lipid | % Yield |
|---|---|---|---|---|---|---|
| 78 |  |  |  |  |  |  |
| 79 | 89.1 | 88.3 | 0.8 | X | X | 62 |
| 80 | 86.2 | 85.4 | 0.8 | X | X | 58 |
| 81 | 81.0 | 80.2 | 0.8 | X | X | 61 |
| 82 | 78.3 | 77.4 | 0.9 | 3.1 | 15.4 | 64 |

IYP Composition (% dsb)

TABLE VII-continued

IYP Composition and Yield Obtained by the Thermal Process
On Further Analysis of Various Yeasts of Table VI

| IYP of Test No. | Protein Crude | Protein Corrected | RNA | Ash | Lipid | % Yield |
|---|---|---|---|---|---|---|
| 83 | 80.4 | 79.3 | 1.1 | 2.9 | 12.3 | 66 |

The primary process is further described in the following Examples Nos. 1–3.

EXAMPLE NO. 1

Preparation of Low RNA-IYP from Saccharomyces cerevisiae

Commercial baker's yeast cream of pH 5.9 and containing 9 percent solids was homogenized by three successive passes through a Manton-Gaulin homogenizer at 8000 psig. The homogenate was diluted with water to 3.4 percent solids, adjusted to pH 9.5, heated at 60° C. for ten minutes, and centrifuged at 14000 rcf × g. into a cell wall residue fraction and an alkaline extract fraction. The alkaline extract contained 79.1 percent of the solids and 92.2 percent of the crude protein (N × 6.25) that was present in the starting yeast.

To 200 ml. of alkaline extract containing 5.8 grams of solids, including 3.92 grams of crude protein and 0.55 grams of nucleic acid, was added sufficient HCl to neutralize the extract to pH 7. The extract at pH 7 was heated at 120° C. for 1 hour, cooled, and separated into an insoluble protein fraction and a supernate containing the majority of the nucleic acids, and a minority of the protein.

The yield of insoluble protein amounted to four pounds per 100 pounds of starting yeast. The composition (dsb) was 85.1 percent crude protein, 2.2 percent nucleic acid.

EXAMPLE NO. 2

Alkaline extract was prepared according to Example No. 1. Twenty gallons of the alkaline extract was charged to a stirred 30 gallon jacketed steel tank and adjusted to pH 7 by the addition of 75 ml. concentrated HCl. The jacket was heated and steam was sprayed into the extract to raise the temperature to 118°–120° C. Samples were removed periodically and centrifuged to obtain the protein. The protein was washed and analyzed.

| Duration of Heating (min.) | 0 | 13 | 28 | 43 | 58 | 73 |
|---|---|---|---|---|---|---|
| Temp. of Extract (° C.) | 40 | 118 | 118 | 118 | 118 | 118 |
| Protein Yield (%)[1] | 84 | 59 | 55 | 54 | 52 | 51 |
| % Crude Protein (dsb) | 91 | 86 | 88 | 87 | 87 | 84 |
| % RNA (dsb) | 13.6 | 2.7 | 1.6 | 1.6 | 1.7 | 1.3 |

[1] protein yield = $100 \times \frac{\text{g. N in recovered protein}}{\text{g. N in heated extract}}$

EXAMPLE NO. 3

Alkaline extract was prepared in accordance with Example No. 1. The alkaline extract was adjusted to pH 6.5 and pumped through a metal coil of dimensions of 40 ft. in length and 0.25 inches in diameter bore immersed in a heated oil bath. The pump rate was adjusted so that the extract was heated at 110°–115° C. for 2 minutes. The heated extract was collected in a flask immersed in an ice bath and centrifuged. The recovered protein was analyzed. The composition (dsb) was: 87 percent crude protein, 3.6 percent RNA. The protein yield as defined in Example No. 2 was 62 percent.

The sterility of the recovered protein was assessed by well-known microbiological testing techniques. The recovered protein was free of microorganisms.

The thermal process of this invention is also applicable to the reduction of the nucleic acid content of isolated proteins having a high content of nucleic acid. This application is shown in Example No. 4.

EXAMPLE NO. 4

Reduction of RNA Content of a Full RNA-IYP

Alkaline extract was prepared from baker's yeast in accordance with Example No. 1. One liter of the alkaline extract containing 2.9 percent total solids was adjusted to pH 4.5 with HCl and centrifuged. The recovered IYP was washed once with water and resuspended to about 5 percent solids. This IYP had the composition (dsb) 81.5 percent crude protein, 13.9 percent RNA, 1.7 percent ash, 13.4 percent lipid, and 3.7 percent carbohydrate. Aliquots (200 ml.) of the 5 percent IYP suspension were adjusted to pH's 5, 6, 7 and 8 with sodium hydroxide, heated for thirty minutes at 118°–120° C., and cooled. The protein was recovered by centrifugation and analyzed.

| Test No. | 84 | 85 | 86 | 87 |
|---|---|---|---|---|
| Process pH | | | | |
| IYP Composition (dsb) | 5 | 6 | 7 | 8 |
| Crude Protein % | 80.3 | 85.2 | 83.9 | 78.7 |
| RNA % | 10.4 | 7.7 | 5.2 | 4.6 |
| Corrected Protein % | 69.7 | 77.3 | 78.6 | 74.0 |
| Ash % | 0.5 | 1.4 | 2.1 | 3.3 |
| Lipid % | 13.8 | 12.1 | 16.0 | 15.4 |

The liquid from the centrifugation contained the remainder of the RNA which was recovered by acidification.

The thermal process of this invention is further applicable to the manufacture of a low RNA-protein product containing the cell walls. That is, the ruptured cells are thermally processed without prior removal of the cell walls. A protein product having a reduced RNA content and containing the cell walls is obtained by separating the insolubles from the solubles after the thermal treatment. This application is shown in Example No. 5.

EXAMPLE NO. 5

Reduction of RNA Content of a Protein Cell Wall Product

An homogenate of baker's yeast was prepared in accordance with Example No. 1. The homogenate was adjusted to pH 7 by the addition of sodium hydroxide.

The homogenate contained 8.2 percent dry solids which were 54.2 percent crude protein. An aliquot of the homogenate was heated for thirty minutes at 118°–120° C. and cooled. The insolubles were recovered by centrifugation and analyzed. The composition (dsb) is set forth in the following table.

| | |
|---|---|
| Crude Protein | 62.4 % |
| RNA | 4.0 % |
| Corrected Protein | 58.3 % |
| Ash | 2.5 % |
| Lipid | 9.1 % |
| Carbohydrate | 26.0 % |

The yeast product contained on a dry solids basis about 28 percent cell fragments of an average fragment size of about 3.8 ± 0.8 by about 2.4 ± 0.7 microns. The cell material is 70–100 percent fragments of irregular shape and 0–30 percent whole cells containing methylene blue stainable material.

The product resulting from applying the thermal process to a mass of ruptured yeast cells from which the cell walls have not been removed has the following composition ranges on a dry solids basis:

| | | | |
|---|---|---|---|
| RNA | 1.5 % | to | 5.0 % |
| Corrected Protein | 55 % % | to | 65 % |
| Ash | 1.5 % | to | 3.5 % |
| Lipid | 6.5 % | to | 9.5 % |
| Carbohydrate | 35.5 % | to | 17 % |
| Fragmented Cell Walls | 20 % | to | 35 % |
| Whole Cells | 0 % | to | 10 % |

What is claimed is:

1. A process for producing a yeast protein product of low nucleic acid content comprising the steps of
   A. rupturing yeast cells to obtain a component containing full nucleic acid protein,
   B. heat treating full nucleic acid protein obtained from step A at a temperature of above 100° C and at pH of about 6–8 for about 10 seconds to about 60 minutes to obtain insoluble protein of reduced nucleic acid content and soluble intact nucleic acid,
   C. separating the insoluble protein of reduced nucleic acid content from the soluble intact nucleic acid.

2. A protein product manufactured according to claim 1 and containing from about 45 to about 65 percent crude protein, about 0.5 to about 9.0 percent nucleic acid on a dry solids basis, about 20 to about 35 percent fragmented cell walls, and 0 to about 10 percent whole cells.

3. The process of claim 1 including the step of recovering the insoluble protein which comprises:
   about 1.5 to about 5.0 percent RNA
   about 55 to about 65 percent corrected protein
   about 1.5 to about 3.5 percent ash
   about 6.5 to about 9.5 percent lipid
   about 35 to about 17 percent carbohydrate
   about 20 to about 35 percent fragmented cell walls
   about 0 to about 10 percent whole cells.

4. A process for treating a yeast product comprising the steps of
   A. rupturing yeast cells,
   B. separating the ruptured cells into a solubles fraction containing the nucleic acid and protein and an insoluble cell wall fraction,
   C. insolubilizing the protein in the solubles fraction by adding acid to the point of minimum protein solubility,
   D. separating the insolubilized protein from the soluble acid whey,
   E. adjusting the pH of the insoluble protein to neutrality and heat treating at a temperature of above 100° C. for up to 60 minutes to obtain an insoluble protein of reduced nucleic acid content and a soluble fraction containing nucleic acid, and
   F. recovering the insoluble protein of reduced nucleic acid content.

5. The process of claim 4 wherein the heat treating is at a pH of about 6 to about 8 and the insoluble protein is recovered in a sterile condition.

6. A process for producing a yeast protein product comprising the steps of
   A. rupturing yeast cells to obtain a soluble fraction containing full nucleic acid protein and an insoluble cell wall fraction,
   B. separating the soluble fraction containing the full nucleic acid protein from the insoluble cell wall fraction,
   C. heat treating soluble fraction obtained from step B at a temperature of above 100° C and at pH of about 6–8 for up to 60 minutes to obtain an insoluble protein of reduced nucleic acid content and a soluble fraction containing intact nucleic acid,
   D. separating the insoluble protein of reduced nucleic acid content from the nucleic acid containing solubles fraction.

7. The process of claim 6 including the step of precipitating intact RNA from the solubles fraction of step D and the step of separating the intact RNA from the remainder of the solubles.

8. The process of claim 6 wherein the yeast cells are ruptured by homogenization below about 50° C.

9. The process of claim 8 wherein the ruptured yeast cells are extracted at a pH between about 5.5 and about 11 and a temperature between about 25° C. and about 60° C. for about 5 to about 60 minutes to solubilize the nitrogenous components of the yeast.

10. The process of claim 6 wherein the heat treating of the soluble fraction is at a temperature of 100° to 120° C. at a pH of 6.5 to 7.5 for one to 30 minutes.

11. The process of claim 6 wherein the heat treating of the soluble fraction is at a temperature of 110°–120° C. at a pH of 6.5 to 7.5 for less than 5 minutes.

12. A process according to claim 6 in which the food grade yeast is selected from the strain of *Saccharomyces cerevisiae* and *Candida utilis*.

13. The process of claim 6 including the step of recovering a yeast protein product comprising:
   about 75 to about 92 percent protein;
   about 0.5 to about 9 percent RNA;
   about 7 to about 15 percent, lipid; about 1 to about 5 percent ash; about 5 to about 20 percent carbohydrate; and about 0 to about 1 percent fiber.

14. The process of claim 13 wherein the recovered yeast protein contains less than about 3 percent RNA.

* * * * *